United States Patent
Takebe et al.

(10) Patent No.: US 12,428,615 B2
(45) Date of Patent: Sep. 30, 2025

(54) MATRIX COMPOSITION

(71) Applicants: Public University Corporation Yokohama City University, Yokohama (JP); Takeda Pharmaceutical Company Limited, Osaka (JP)

(72) Inventors: Takanori Takebe, Tokyo (JP); Norikazu Saiki, Tokyo (JP)

(73) Assignees: Public University Corporation Yokohama City University, Kanagawa (JP); Takeda Pharmaceutical Company Limited, Osaka (JP)

( * ) Notice: Subject to any disclaimer, the term of this patent is extended or adjusted under 35 U.S.C. 154(b) by 994 days.

(21) Appl. No.: 17/599,458

(22) PCT Filed: Mar. 27, 2020

(86) PCT No.: PCT/JP2020/013882
§ 371 (c)(1),
(2) Date: Sep. 28, 2021

(87) PCT Pub. No.: WO2020/203713
PCT Pub. Date: Oct. 8, 2020

(65) Prior Publication Data
US 2022/0195367 A1 Jun. 23, 2022

(30) Foreign Application Priority Data
Mar. 29, 2019 (JP) ................. 2019-066048

(51) Int. Cl.
*C12M 1/12* (2006.01)
*C12M 3/00* (2006.01)
*C12N 5/071* (2010.01)

(52) U.S. Cl.
CPC ............ *C12M 25/14* (2013.01); *C12M 21/08* (2013.01); *C12N 5/0676* (2013.01); *C12N 5/069* (2013.01)

(58) Field of Classification Search
None
See application file for complete search history.

(56) References Cited

U.S. PATENT DOCUMENTS

| | | |
|---|---|---|
| 2005/0106717 A1 | 5/2005 | Wilson et al. |
| 2011/0318319 A1 | 12/2011 | Hargrave et al. |
| 2014/0289877 A1 | 9/2014 | Taniguchi et al. |
| 2015/0284689 A1 | 10/2015 | Nigam |
| 2017/0360551 A1 | 12/2017 | Liu |
| 2018/0030409 A1 | 2/2018 | Lewis et al. |
| 2018/0352792 A1 | 12/2018 | Taniguchi et al. |
| 2019/0119628 A1 | 4/2019 | Jones |
| 2020/0164109 A1* | 5/2020 | Kroll ............ A61L 27/28 |
| 2020/0263129 A1 | 8/2020 | Dunbar et al. |
| 2020/0283735 A1 | 9/2020 | Ionis |
| 2021/0355438 A1 | 11/2021 | Fan et al. |

FOREIGN PATENT DOCUMENTS

| | | |
|---|---|---|
| CN | 1673360 A | 9/2005 |
| CN | 101120083 A | 2/2008 |
| CN | 105985925 A | 10/2016 |
| CN | 107427537 A | 12/2017 |
| CN | 108368484 A | 8/2018 |
| CN | 108456659 A | 8/2018 |
| CN | 109415696 A | 3/2019 |
| CN | 111148829 A | 5/2020 |
| JP | 2012-508771 A | 4/2012 |
| WO | WO-2013/047639 A1 | 4/2013 |
| WO | WO-2016/035777 A1 | 3/2016 |
| WO | WO-2016/141137 A1 | 9/2016 |
| WO | WO-2017/205511 A1 | 11/2017 |
| WO | WO-2018/085615 A1 | 5/2018 |
| WO | WO-2018/094522 A1 | 5/2018 |
| WO | WO-2018/229251 A | 12/2018 |
| WO | WO-2019/060518 A1 | 3/2019 |
| WO | WO-2019/066059 A1 | 4/2019 |

OTHER PUBLICATIONS

Chen et al., "Controlled assembly of heterotypic cells in a core-shell scaffold: organ in a droplet," Lab on a Chip, Apr. 21, 2016, 16(8):1346-1349.
Garnier et al., "Expansion of human primary hepatocytes in vitro through their amplification as liver progenitors in a 3D organoid system," Scientific Reports, May 29, 2018, 8(1):1-10.
Matsusaki et al., "Three-Dimensional Human Tissue Chips Fabricated by Rapid and Automatic Inkjet Cell Printing," Advanced Healthcare Materials, Apr. 2013 (online Nov. 2, 2012), 2(4):534-539.
Supplemental European Search Report dated Dec. 23, 2022 in EP 20783389.8.
Yamada et al., "Controlled formation of heterotypic hepatic microorganoids in anisotropic hydrogel microfibers for long-term preservation of liver-specific functions," Biomaterials, Nov. 2012 (online Aug. 17, 2012), 33:8304-8315.
Zhang et al., Layered hydrogels accelerate iPSC-derived neuronal maturation and reveal migration defects caused by MeCP2 dysfunction.
Office Action dated Mar. 21, 2024 in CN 202080025294.7, with English translation.
Alves-Lopes et al., "Use of a three-layer gradient system of cells for rat testicular organoid generation," Nature Protocols, Jan. 4, 2018, 13(2):248-259.

(Continued)

*Primary Examiner* — Nghi V Nguyen
(74) *Attorney, Agent, or Firm* — Foley & Lardner LLP (57) ABSTRACT

The present invention provides means for producing an organoid close to an organ in a living body and capable of secretion of a plasma protein and immune response. A matrix composition of the present invention provided as such means includes: (1) a first matrix containing one or more cells selected from the group consisting of vascular cells, nerve cells, and blood cells; and (2) a second matrix containing to cells constituting an organ and/or an organoid, in which the first matrix envelops the second matrix, and the first matrix has at least one opening.

10 Claims, 1 Drawing Sheet

(56) References Cited

OTHER PUBLICATIONS

International Search Report dated Jun. 16, 2020 in PCT/JP2020/013882.
Nahmias et al., "Endothelium-Mediated Hepatocyte Recruitment in the Establishment of Liver-like Tissue In Vitro," Tissue Engineering, Jul. 17, 2006, 12(6):1627-1638.
Nio et al., "Application to blood coagulation disease using iPS liver organoid (non-official translation)," Abstracts of the 18th Congress of the Japanese Society for Regenerative Medicine, Feb. 22, 2019, p. 03-093, 2 pages.
Takebe et al., "State of the art of liver organoid generation toward transplant application," Japanese Journal of Transplantation, 2017, 52(4,5):310-317.
Taniguchi, H., "Vascularized and functional human liver from an iPSC-derived organ bud transplant," Prog. Med., 2017, 37(5):565-569.
Office Action and Search Report dated May 30, 2022 in CN 202080025294.7, with English translation.
Notice of Allowance dated Mar. 21, 2024 in CN 202080025294.7, with English translation.
Office Action dated Feb. 6, 2024 in JP 2021-511963, with English translation.
Office Action dated Jun. 30, 2025 in KR 10-2021-7028106, with English translation.

* cited by examiner

MATRIX COMPOSITION

CROSS-REFERENCE TO RELATED APPLICATIONS

This application is the U.S. National Stage of PCT/JP2020/013882, filed Mar. 27, 2020, which claims priority to JP 2019-066048, filed Mar. 29, 2019.

TECHNICAL FIELD

The present invention relates to a matrix composition containing cells or an organoid. More particularly, the present invention relates to a matrix composition having a specific structure formed by a plurality of matrices containing cells and the like. The present invention also relates to a production method and use of such a matrix composition.

BACKGROUND ART

Aiming to develop medicaments for diseases of various organs including liver and pancreas and realize regenerative medicine, research and development have been conducted to produce a cell structure obtained by self-assembly of cultured cells to reproduce a three-dimensional structure of each organ or a complicated structure of a blood vessel, a bile duct or another vessel, namely, an organoid. As an advanced cell structure of such an organoid, an anlage of an organ formed at an early stage of development, namely, an organ bud (such as a germ corresponding to an organ bud of liver) can be produced by culturing a combination of specific types of cells including an undifferentiated cell. Such an organoid or the like that can be designated also as a "mini-organ" is, as compared with conventional cells and the like of an organ each singly cultured, highly useful because it can be used as an evaluation system closer to a living body in evaluation of drug efficacy or toxicity, and in addition, can be used in a transplant operation or production of a plasma protein.

Patent Literature 1 describes that a three-dimensional structure designated as an "organ bud" (for example, a liver bud or a pancreatic bud) can be produced by seeding and culturing a cell mixture obtained by mixing, in a prescribed ratio, vascular endothelial cells, mesenchymal cells (for example, mesenchymal stem cells) and organ cells (for example, liver endoderm cells or pancreatic β cells) "under special circumstances where cells are supported by extracellular matrix components", specifically, for example, on Matrigel fixed in a culture vessel. On the other hand, Patent Literature 1 describes (particularly in Examples 1 and 2) that "no three-dimensional (conformational) structure formed" when the cell mixture was "embedded in Matrigel".

Non Patent Literature 1 describes a testicular organoid (matrix composition) having a form (three-layer gradient system) in which a second matrix ("Matrigel", Corning Incorporated) containing testicular cells mixed therein is enveloped by a first matrix not containing cells, and an opening of the first matrix is sealed with a third matrix not containing cells. In the system described in this literature, the first and third matrices do not contain cells to cause a gradient of a cell density, and thus, formation of an organoid is accelerated by the testicular cells contained in the second matrix. Non Patent Literature 1 does not describe, however, that other cells (organoid) different from the testicular cells are cultured in the system, and that a matrix excluding the second matrix contains cells.

Non Patent Literature 2 describes the following: When each of (1) an organoid produced from a human microvessel endothelial cells (MVECs) and hepatocytes (liver cells), (2) an organoid produced from human umbilical-vein endothelial cells (HUVECs) and hepatocytes (liver cells), (3) an organoid produced from rat liver sinusoidal endothelial cells (LSECs) and hepatocytes (liver cells), and (4) an organoid produced from human umbilical-vein endothelial cells (HUVECs), normal human dermal fibroblast (NHDFs) and hepatocytes (liver cells) was (two-dimensionally) cultured on Matrigel applied on a slide, a network of vascular endothelial cells disrupted in the end in the organoids (2) and (3), but survived in the organoids (1) and (4), and eventually formed a capsule of fibroblasts which was free-floating from the slide. Non Patent Literature 2 does not describe, however, that such cells or an organoid is cultured in Matrigel (having a layered structure).

Non Patent Literature 3 describes the following: When a structure including a lower gel layer containing neural progenitor cells (NPCs) and an upper gel layer containing NPCs, astrocytes or neurons is cultured, particularly when the upper gel layer contains astrocytes, the NPCs of the lower gel layer migrate toward the upper layer, and differentiation from the NPCs into nerve cells is accelerated. Non Patent Literature 3, however, neither discloses nor suggests that the lower gel layer "is enveloping" the upper gel layer and that the lower gel layer "has at least one opening".

CITATION LIST

Patent Literature

Patent Literature 1: WO2013/047639

Non Patent Literature

Non Patent Literature 1: Nature protocols, Vol. 13, No. 2, 2018, 248-259
Non Patent Literature 2: TISSUE ENGINEERING, 12(6), 2006, pp. 1627-1638
Non Patent Literature 3: PNAS 113 (12) 3185-3190

SUMMARY OF INVENTION

Technical Problem

An object of the present invention is to provide means for producing an organoid close to an organ in a living body and capable of secretion of a plasma protein and immune response.

Solution to Problem

The present inventors found that an organoid closer to an organ in a living body than a conventional one is formed by embedding different types of cells and the like in respective layers of a matrix having a layered structure, and culturing the cells and the like contained in the resultant matrix layered structure on a gas-liquid interface. Specifically, it was found that a matrix layered structure including a second matrix containing cells constituting an organ (preferably, cells capable of forming an organoid) or an organoid itself, and a first matrix that envelopes the second matrix excluding a part (an opening) thereof, and contains vascular cells (such as vascular endothelial cells or smooth muscle cells), nerve cells, blood cells or the like is produced; and with oxygen or the like supplied to the cells or the like contained in the second matrix through the opening, culture is performed with the first matrix and the second matrix immersed in a liquid medium, so that an organoid in which the cells contained in the first matrix forms a hierarchical cell network to be integrated with the cell contained in the second matrix can be formed. It was found that such a matrix layered structure (that can be designated also as a matrix composition containing cells or an organoid, a matrix, and the like) can be used for purposes expected to an organoid such as production of a plasma protein and the like. Thus, the present invention was accomplished.

Specifically, for solving the above-described problems, the present invention provides the following [1] to [10]:

[1] A matrix composition, comprising: (1) a first matrix containing one or more cells selected from the group consisting of vascular cells, nerve cells, and blood cells; and (2) a second matrix containing cells constituting an organ and/or an organoid, wherein the first matrix envelops the second matrix, and the first matrix has at least one opening.

[2] The matrix composition according to item 1, wherein the matrix composition has a hierarchical cell network.

[3] The matrix composition according to item 1, wherein the vascular cells contained in the first matrix is hemogenic endothelial cells.

[4] The matrix composition according to item 1, wherein the cells constituting an organ contained in the second matrix is a combination of liver endoderm cells, vascular endothelial cells and mesenchymal stem cells, or a combination of pancreatic β cells, vascular endothelial cells and mesenchymal stem cells.

[5] A production method for a matrix composition, comprising the steps of: (a) suspending, in a second matrix in a fluid form, cells constituting an organ and/or an organoid, and solidifying the second matrix; and (b) suspending, in a first matrix in a fluid form, cells selected from the group consisting of vascular cells, nerve cells and blood cells, covering the second matrix with the first matrix in such a manner that the first matrix has at least one opening, and solidifying the first matrix.

[6] The production method according to item 5, further comprising a step of: (c) immersing, in a liquid medium, the matrix composition in a state of being suspended from a breathable membrane for culturing, with gas exchange through the breathable membrane ensured, to cause the cells constituting an organ contained in the second matrix to form a conformational structure.

[7] A production method for a chimeric non-human animal, comprising transplanting the matrix composition according to item 1 or the matrix composition produced by the method according to item 5 in a chimeric non-human animal for differentiation into a tissue or an organ.

[8] A chimeric non-human animal produced by the method according to item 7.

[9] A culture system, comprising: a matrix composition suspended from a breathable membrane; and a liquid medium in which the matrix composition is immersed, wherein the matrix composition contains: (1) a first matrix containing one or more cells selected from the group consisting of vascular cells, nerve cells, and blood cells; and (2) a second matrix containing cells constituting an organ and/or an organoid, the first matrix envelops the second matrix, and the first matrix has at least one opening.

[10] A production method for a plasma protein, comprising the steps of: (1) culturing the matrix composition according to item 1; and (2) collecting a culture supernatant from a cultured product cultured in the step (1).

Advantageous Effects of Invention

A matrix composition provided by the present invention has a hierarchical cell network (such as a vascular structure) close to an organ in a living body and can be regarded as a novel type of organoid integrally with a matrix supporting a cell or an organoid. By using such a matrix composition, preferably by producing a chimeric non-human animal to which the matrix composition has been transplanted, it is possible to improve reliability of prediction of a drug metabolism profile in a human, evaluation of drug efficacy, evaluation of toxicity, and evaluation of drug interaction.

DESCRIPTION OF EMBODIMENT

Definition

—Vascular Endothelial Cell

The term "vascular endothelial cell" used herein is a term encompassing concepts of both a hemogenic endothelial cell (HEC) and a non-hemogenic endothelial cell (non-HEC). An HEC is a vascular endothelial cell capable of producing a hematopoietic stem cell (having hematopoietic ability) and is designated also as a hematopoietic type vascular endothelial cell. On the other hand, a non-HEC is a vascular endothelial cell not having such hematopoietic ability.

The vascular endothelial cell used in the present invention may be a high purity cell population of vascular endothelial cells collected from a living body (for example, microvessel endothelial cells (MVECs), liver sinusoidal endothelial cells (LSECs), umbilical-vein endothelial cells (UVECs) or the like), or may be a high purity cell population of vascular endothelial cells obtained by differentiating pluripotent stem cells such as ES cells or iPS cells, or other cells having differentiation ability into vascular endothelial cells. The high purity cell population of vascular endothelial cells contain vascular endothelial cells at 70% or more, 80% or more, 90% or more, 95% or more, or 99% or more with respect to whole cells contained in the cell population.

—Hemogenic Endothelial Cell (HEC)

The term "hemogenic endothelial cell (HEC)" used herein means a vascular endothelial cell having hematopoietic ability that is CD34-positive and CD73-negative for a cell marker of the HEC. The HEC used in the present invention may include a precursor cell thereof. Representative examples of such a precursor cell include cells present in the differentiation process from a precursor cell of a vascular endothelial cell positive for a cell marker Flk-1 (CD309, KDR) (for example, a lateral plate mesoderm cell) to the HEC (see Cell Reports 2, 553-567, 2012). It is noted that a precursor cell obtained at an early stage of differentiation such as one positive for Flk-1 (CD309, KDR) is a precursor cell common between the HEC and the non-HEC, and hence, the term "HEC precursor cell" embraces a precursor cell common between the HEC and the non-HEC unless otherwise stated.

The hemogenic endothelial cells (HECs) used in the present invention may be a high purity cell population of HECs collected from a living body, or may be a high purity cell population of HECs obtained by differentiating pluripotent stem cells such as ES cells or iPS cells, or other cells having differentiation ability into vascular endothelial cells (for example, lateral plate mesoderm cells). The high purity cell population of HECs contain HECs and/or HEC precursor cells at 70% or more, 80% or more, 90% or more, 95% or more, or 99% or more with respect to whole cells contained the cell population. In one embodiment, the high purity cell population of HECs contain HECs at 70% or more, 80% or more, 90% or more, 95% or more, or 99% or more with respect to whole cells contained in the cell population.

A method for differentiating, into a hemogenic endothelial cell (HEC), a pluripotent stem cell such as an ES cell or an iPS cell, or another cell having differentiation ability into a vascular endothelial cell is known, and differentiation from, for example, an iPS cell can be performed in accordance with a method described in PLoS One, 2013; 8(4): e59243, Nat Biotechnol. 2014; 32(6): 554-61, Sci Rep. 2016; 6: 35680, or the like.

—Non-Hemogenic Endothelial Cell (Non-HEC)

The term "non-hemogenic endothelial cell (non-HEC)" used herein means a vascular endothelial cell that has no hematopoietic ability and is CD31-, CD73- and CD144-positive for cell markers of the non-HEC. The non-HEC used in the present invention may include a precursor cell thereof. Representative examples of such a precursor cell include cells present in the differentiation process from a precursor cell of a vascular endothelial cell positive for a cell marker Flk-1 (CD309, KDR) (for example, a lateral plate mesoderm cell) to the non-HEC (see Cell Reports 2, 553-567, 2012). It is noted that a precursor cell obtained at an early stage of differentiation such as one positive for Flk-1 (CD309, KDR) is a precursor cell common between the HEC and the non-HEC, and hence, the term "non-HEC precursor cell" embraces a precursor cell common between the HEC and the non-HEC unless otherwise stated.

The non-hemogenic endothelial cells (non-HEC) used in the present invention may be a high purity cell population of non-HECs collected from a living body, or may be a high purity cell population of non-HECs obtained by differentiating pluripotent stem cells such as ES cells or iPS cells, or other cells having differentiation ability into vascular endothelial cells (for example, lateral plate mesoderm cells). The high purity cell population of non-HECs contain non-HECs and/or non-HEC precursor cells at 70% or more, 80% or more, 90% or more, 95% or more, or 99% or more with respect to whole cells contained the cell population. In one embodiment, the high purity cell population of non-HECs contain non-HECs at 70% or more, 80% or more, 90% or more, 95% or more, or 99% or more with respect to whole cells contained in the cell population.

A method for differentiating, into a non-hemogenic endothelial cell (non-HEC), a pluripotent stem cell such as an ES cell or an iPS cell, or another cell having differentiation ability into a vascular endothelial cell is known, and differentiation from, for example, an iPS cell can be performed in accordance with a method described in Nat Cell Biol. 2015; 17(8): 994-1003, Cell Rep. 2017, 21(10): 2661-2670, or the like.

—Mesenchymal Cell

The term "mesenchymal cell" used herein refers to a connective tissue cell present in a connective tissue mainly derived from a mesoderm, and forming a support structure for a cell functioning in the tissue, and is a term encompassing concepts of both a differentiated cell (differentiated mesenchymal cell) and a cell fated to differentiate into a mesenchymal cell but not yet differentiated into a mesenchymal cell (undifferentiated mesenchymal cell), namely, what is called a mesenchymal stem cell. It is noted that the "vascular endothelial cell" is a kind of a cell differentiated from an undifferentiated mesenchymal cell, but is herein excluded from the definition of the "mesenchymal cell".

It can be determined whether a given cell is an undifferentiated mesenchymal cell or a differentiated mesenchymal cell depending on, for example, whether or not it is positive for one of or two or more of undifferentiated mesenchymal cell markers, Stro-1, CD29, CD44, CD73, CD90, CD105, CD133, CD271, Nestin and the like (when positive, it is determined as an undifferentiated mesenchymal cell, and when negative, it is determined as a differentiated mesenchymal cell).

The mesenchymal cell may express a cell marker specific to a specific organ (tissue) in accordance with an organoid aimed by the present invention or a "cell constituting an organ" to be used in combination. Examples of such a cell marker include FOXF1, COL4A and ALCAM corresponding to cell markers of a septum transversum mesenchyme (STM).

—Hepatocyte

The term "hepatocyte" (liver cell) used herein refers to a parenchymal cell of liver, and is a term encompassing concepts of both a differentiated hepatocyte (hepatocyte that has been differentiated) and a cell fated to differentiate into a hepatocyte but not yet differentiated into a hepatocyte (undifferentiated hepatocyte), namely, what is called a liver precursor cell (for example, a liver endoderm cell). The differentiated hepatocyte may be a cell collected from a living body (isolated from the liver in a living body), or may be a cell obtained by differentiating a pluripotent stem cell such as an ES cell or an iPS cell, a liver precursor cell, or another cell having differentiation ability into a hepatocyte. The undifferentiated hepatocyte may be collected from a living body, or may be a cell obtained by differentiating a pluripotent stem cell such as an ES cell or an iPS cell, or another stem cell or a precursor cell. A cell that can be differentiated into a hepatocyte can be produced in accordance with, for example, K. Si-Taiyeb, et al., Hepatology, 51(1): 297-305 (2010), or T. Touboul, et al., Hepatology 51(5): 1754-65 (2010). A method for differentiating, into a liver cell, a pluripotent stem cell such as an ES cell or an iPS cell, a liver precursor cell or another cell having differentiation ability into a liver cell is known, and the differentiation from, for example, an iPS cell can be performed in accordance with a method described in Hepatology, 2010; 51(1): 297-305, Cell Rep. 2017; 21(10): 2661-2670, or the like. In using either of (particularly, the latter of) a cell population collected from a living body and a cell population produced by differentiation induction from ES cells, iPS cells or the like, a high purity cell population of differentiated hepatocytes or a high purity cell population of undifferentiated hepatocytes may be used, or a cell mixture containing differentiated hepatocytes and undifferentiated hepatocytes in an arbitrary ratio may be used.

It can be determined whether or not a given cell is a differentiated liver cell depending on whether or not expression of one of, or two or more of mature hepatocyte markers such as asialoglycoprotein receptor 1 (ASGR1), α-fetoprotein (AFP) which is an immature hepatocyte marker (early liver differentiation marker), albumin (ALB) which is an early liver differentiation marker, retinol-binding protein (RBP4), transthyretin (TTR), glucose-6-phosphatase (G6PC) and the like is positive. On the other hand, it can be determined whether or not a given cell is an undifferentiated liver cell depending on whether or not expression of one of, or two or more of cell markers such as HHEX, SOX2, HNF4α, AFP and ALB is positive.

—Cell Marker

The term "cell marker" used herein is a gene which is specifically expressed in a prescribed cell type (positive marker) or a gene which is not specifically expressed in a prescribed cell type (negative marker), and specifically refers to a substance generated (positive marker) or not generated (negative marker) as an mRNA through transcription of the gene included in a genome, or as a protein resulting from translation of the mRNA. The cell marker can be preferably labelled (stained) with a fluorescent substance, and is a protein expressed on a cell surface (cell surface marker) easily capable of detection, concentration, isolation and the like of a cell expressing the cell marker.

That a marker gene is "positive" means that expression level of an mRNA of the gene or a protein can be detected by a method usual for or known to those skilled in the art, or is higher than a prescribed threshold value (such as a background level). That a marker gene is "negative" means that the expression level of an mRNA of the gene or a protein cannot be detected by a method usual for or known to those skilled in the art, or is lower than a prescribed threshold value (such as a background level).

It can be determined whether a cell marker is positive or negative by a method usual for or known to those skilled in the art, or based on a qualitative or quantitative result. A cell marker in the form of a protein can be detected or measured for the expression level by utilizing an immunoassay using an antibody specific to the protein, such as ELISA, immunostaining, or flowcytometry. A cell marker in the form of an mRNA can be detected or measured for the expression level by utilizing an assay using a nucleic acid specific to the mRNA, such as RT-PCR (including quantitative PCR), a microarray, or a biochip.

—Matrix Composition—

Figure 1:
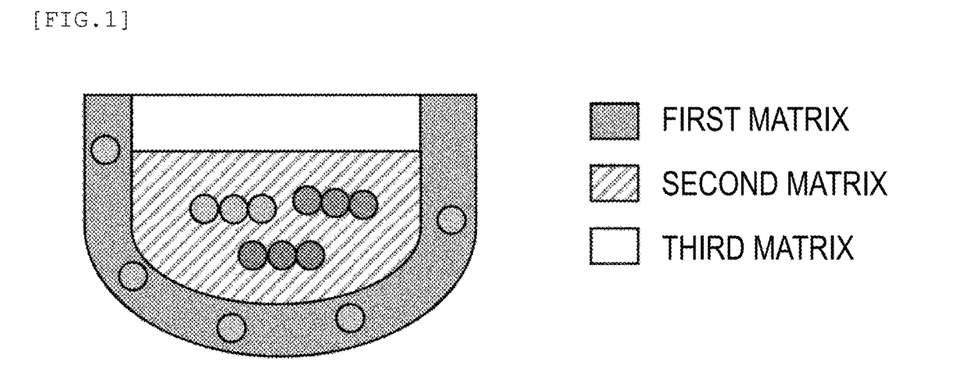
FIG. 1 is a schematic diagram illustrating an example of an embodiment of the present invention.

A matrix composition of the present invention includes (1) a first matrix containing one or more cells selected from the group consisting of vascular cells, nerve cells, and blood cells, and (2) a second matrix containing cells constituting an organ and/or an organoid, and has a structure in which the first matrix envelopes the second matrix, and the first matrix has at least one opening (see FIG. 1).

The "opening" of the first matrix refers to a portion not enveloping the second matrix. In other words, through the "opening", the second matrix can receive, from the outside, oxygen, nutrient, and another substance necessary for cells contained in the second matrix directly or indirectly via a "substance alternative to the first matrix". When the second matrix is wholly enveloped by the first matrix, the cells constituting an organ or the like contained in the second matrix cannot receive, from the outside, sufficient amounts of oxygen, nutrient and the like because of the vascular cells or the like contained in the first matrix or a network formed therefrom. The "opening" provided in the first matrix is means for avoiding such a problem, and as long as this purpose is achieved, the "opening" may be closed by the "substance alternative to the first matrix".

A representative example of the "substance alternative to the first matrix" includes a "matrix not containing cells" (herein designated as the "third matrix"). In other words, in one embodiment, the matrix composition of the present invention is a matrix composition including a first matrix containing vascular cells or the like, a second matrix containing cells constituting an organ or the like, and a third matrix not containing cells, the first matrix and the third matrix envelope the second matrix, the first matrix has at least one opening, and a part or the whole of the opening is filled with the third matrix.

The term "matrix" used herein refers to a preparation including an extracellular matrix (ECM) and an additive component such as a growth factor added if necessary to be used for culturing cells constituting an organ or to be used in three-dimensional cell culture for forming an organoid. Various types of such a matrix are known, and an appropriate one of these can be selected and used depending on purposes of the present invention.

The ECM included as a component of the matrix basically contains a fibrous protein and proteoglycan as principal components, and examples of such components include elastin, entactin, osteonectin, collagen (such as type IV collagen), tenascin, thrombospondin, perlecan, vitronectin, fibrillin, fibronectin, heparin (sulfate) proteoglycan, and laminin.

Examples of the growth factor added to the matrix if necessary include EGF, PDGF, IGF-1, TGF-β, and VEGF.

A matrix containing the ECM and the growth factor is commercially available, and examples include "BD Matrigel" (BD Biosciences) and Matrigel (Corning).

The composition and the concentration (whether it is undiluted or diluted) of the matrix can be appropriately adjusted depending on purposes of the present invention by those skilled in the art. For example, Matrigel can be used, if necessary, in the form of a mixture with a liquid medium in order to increase handleability and attain proper hardness when solidified. As the liquid medium to be mixed with Matrigel in such an embodiment, those the same as a liquid medium for immersing and culturing a matrix composition used in a production method for a matrix composition separately described herein can be used.

Matrigel is generally in the form of a fluid at a low temperature (for example, 4° C. or lower), but is solidified into a gel at ordinary temperature or higher (for example, 37° C. or higher). A matrix containing prescribed cells or the like is generally obtained by mixing Matrigel in a fluid state with the prescribed cells or the like, heating the resultant and allowing the resultant to stand to solidify.

Besides, a self-assembly peptide known as a hydrogel, for example, a hydrogel containing arginine, glycine and asparagine can be used as a component of the matrix in the present invention. When a matrix containing such a hydrogel is used, a necessary ionic solution or ionic molecule may be added in solidification.

The first, the second (and the arbitrarily used third) matrices of the present invention may be the same preparation, or may be different preparations. For example, differentiation of cells and formation of an organoid (for example, an organ bud) contained in a matrix may be changed in some cases depending on a growth factor added to the matrix or hardness of the matrix, and therefore, an appropriate matrix may be used in accordance with an embodiment of the present invention.

—First Matrix

The first matrix contains one or more cells selected from the group consisting of vascular cells, nerve cells and blood cells. Species from which these cells are derived is not especially limited, and may be a human, or an animal excluding a human, for example, a mammal such as a mouse, a rat, a dog, a pig or a monkey.

Examples of the vascular cell include a vascular endothelial cell, a blood vessel smooth muscle cell, and a pericyte.

For example, a vascular endothelial cell is preferably used as the cell (vascular cell) contained in the first matrix from the viewpoints that it can impart a hierarchical microvessel structure to an organoid of the liver, pancreas or the like contained in the second matrix to obtain a suitable model of a vascular disease (for example, sinusoidal obstruction syndrome). Besides, among vascular endothelial cells, a hemogenic endothelial cell is more preferred because it forms a hierarchical microvessel structure and can produce a blood cell (for example, an immunocompetent cell such as a macrophage or a neutrophil).

The HECs used in the present invention may be a high purity cell population of HECs collected from a living body, or may be a high purity cell population of HECs obtained by differentiating pluripotent stem cells such as ES cells or iPS cells, or other cells having differentiation ability into a vascular endothelial cells (for example, lateral plate mesoderm cells). A method for differentiating, into a hemogenic endothelial cell (HEC), a pluripotent stem cell such as an ES cell or an iPS cell, or another cell having differentiation ability into a vascular endothelial cell is known, and differentiation from, for example, an iPS cell can be performed in accordance with a method described in PLoS One, 2013; 8(4): e59243, Nat Biotechnol. 2014; 32(6): 554-61, Sci Rep. 2016; 6: 35680, or the like. A "high purity" cell population of HECs contains HECs and/or HEC precursor cells at 70% or more, 80% or more, 90% or more, 95% or more, or 99% or more with respect to whole cells contained in the cell population.

Examples of the nerve cell include a GABAergic neuron, a dopaminergic neuron, and a motor neuron.

The blood cells (hematopoietic cells) are roughly divided into a platelet, an erythrocyte and a leukocyte. Examples of the leukocyte include a lymphocyte (an NK cell, a T lymphocyte, a B lymphocyte, a macrophage or a dendritic cell), a monocyte, an eosinophil, a basophil and a neutrophil. For example, an immunocompetent cell such as a macrophage or a neutrophil is preferable as the cell (hematopoietic cell) contained in the first matrix from the viewpoint that a matrix composition usable as a pathological model of an inflammatory disease or the like can be produced using it.

Hardness of the first matrix can be appropriately adjusted in consideration of permeability of, for example, oxygen supplied from a gas phase, or a substance such as a component supplied from a liquid medium, and another action on growth of cells contained in the first matrix, and can be set to, for example, a range of 0.05 to 50 kPa. It is noted that an index of this "hardness" can be appropriately converted into a dilution rate in diluting Matrigel with a medium, or a concentration of an ECM in the matrix. Besides, a thickness of the first matrix, an area of a contact surface with the second matrix and the like can be appropriately adjusted in consideration of items similar to those described above.

—Second Matrix

The second matrix contains cells constituting an organ and/or an organoid. Species from which the cell or organoid is derived is not especially limited, and may be a human, or an animal excluding a human, for example, a mammal such as a mouse, a rat, a dog, a pig or a monkey.

The second matrix encompasses the following embodiments (i) to (iii):

(i) An embodiment in which the second matrix contains cells constituting an organ, particularly one, or two or more cells capable of forming an organoid in a state where an organoid is not yet formed (for example, by a step (a) of a production method for a matrix composition of the present invention);

(ii) an embodiment in which the second matrix contains an organoid having been separately formed (for example, by the step (a) of the production method for a matrix composition of the present invention); and (iii) an embodiment in which the second matrix contains an organoid resulting from culturing (for example, by a step (c) of the production method for a matrix composition of the present invention) one, or two or more cells (including at least a "cells constituting an organ") capable of forming an organoid contained in the second matrix (for example, by a step (a) of a production method for a matrix composition of the present invention).

—Cell Constituting Organ

The term "cell constituting an organ" used in the present invention encompasses (I) a parenchymal cell constituting an organ, and (II) a non-parenchymal cell constituting an organ. Besides, each of (I) the parenchymal cell and (II) the non-parenchymal cell encompasses (i) a cell having a prescribed functionality as a differentiated mature or terminally differentiated parenchymal or non-parenchymal cell (herein, simply referred to as the "differentiated cell"), and (ii) a cell having differentiation ability into a parenchymal cell or a non-parenchymal cell, or fated to differentiate (committed) but not differentiated yet, or in a stage of a stem cell or a precursor cell and not sufficiently having a prescribed functionality as a parenchymal cell or non-parenchymal cell (herein, simply referred to as the "undifferentiated cell").

As the cells constituting an organ, at least one cell selected from the group consisting of a differentiated cell of a parenchymal cell, an undifferentiated cell of a parenchymal cell, a differentiated cell of a non-parenchymal cell, and an undifferentiated cell of a non-parenchymal cell, and preferably a combination of two or more cells capable of forming an "organoid" (for example, an organ bud) can be used. The types of and culturing conditions for cells necessary for forming various organoids (for example, an organ bud) are known, which can be applied to the present invention (the second matrix).

Examples of the "organ" include the liver, pancreas, kidney, heart, lung, spleen, esophagus, stomach, thyroid gland, parathyroid gland, thymus, gonad, brain, and spinal cord.

Examples of a "parenchymal cell" constituting an organ include a hepatocyte of the liver, an endocrine cell (for example, an α cell, a β cell, a δ cell, an ε cell or a PP cell) and a pancreatic duct epithelial cell of the pancreas, a tubular epithelial cell and a glomerulosa epithelial cell of the kidney, an alveolar epithelial cell of the lung, a cardiac muscle cell of the heart, an epithelial cell of the intestinal tract, a nerve cell and a glial cell of the brain, and a nerve cell and a Schwann cell of the spinal cord.

Examples of a "non-parenchymal cell" constituting an organ include a sinusoidal endothelial cell, a liver stellate cell and a Kupffer cell of the liver, a pancreatic stellate cell and a pancreatic microvascular endothelial cell of the pancreas, a renal glomerular endothelial cell of the kidney, a pulmonary artery endothelial cell and a lung fibroblast of the lung, heart microvascular endothelial cell, an aortic endothelial cell, a coronary endothelial cell and a heart fibroblast of the heart, an intestinal microvascular endothelial cell of the intestinal tract, and a brain microvascular endothelial cell, a vascular pericyte, a choroid endothelial cell and a brain adventitia fibroblast of the brain.

Examples of an "undifferentiated organ cell" having differentiation ability into a parenchymal cell or non-parenchymal cell constituting an organ include cells capable of differentiating into ectodermal organs such as the brain, spinal cord, adrenal medulla, epidermis, hair or nail or skin gland, a sense organ, a peripheral nerve and a crystalline lens; cells capable of differentiating into mesodermal organs such as the kidney, ureter, heart, blood, gonad, adrenal cortex, muscle, skeleton, dermis, connective tissue and mesothelium; and cells capable of differentiating into endodermal organs such as the liver, pancreas, intestinal tract, lung, thyroid gland, parathyroid gland and urinary tract.

—Organoid

The term "organoid" refers to an artificial tissue structure (three-dimensional structure) similar to an organ, and various types of organoids, such as organoids of the liver, pancreas, kidney, heart, lung, spleen, esophagus, stomach, thyroid gland, parathyroid gland, thymus, gonad, brain, and spinal cord are already known (see, for example, https://www.nejm.org/doi/pdf/10.1056/NEJMra1806175, https://www.nature.com/articles/s41568-018-0007-6 and http://www.amsbio.com/brochures/organoid-culture-handbook.pdf). In the present invention, an arbitrary organoid can be used to be contained in the second matrix. It is noted that the term "organoid" encompasses an "organ bud" (for example, a liver bud or a pancreatic bud) corresponding to a structure obtained at an early stage finally toward an organ having a complicated structure.

A representative example of the organoid of the present invention includes a "liver organoid". A production method for a liver organoid is known, and as the liver organoid used in the present invention, liver organoids obtained by various known production methods can be used.

The liver organoid is preferably a "liver bud". A production method for a liver bud is also known, and for example, as described in Patent Literature 1 mentioned above, a liver bud can be produced from a combination of liver endoderm cells, vascular endothelial cells and mesenchymal stem cells. It is noted that a liver endoderm cell corresponds to an undifferentiated cell of a parenchymal cell used herein, and a vascular endothelial cell and a mesenchymal stem cell correspond to an undifferentiated cell of a non-parenchymal cell used herein. As a vascular endothelial cell used in production of a liver organoid (for example, a liver bud), a non-hemogenic endothelial cell (non-HEC) is preferred.

In one embodiment of the present invention, when a liver organoid or a liver bud is selected as the organoid, or when a combination of liver endoderm cells, vascular endothelial cells and mesenchymal stem cells, or a combination of cells for producing another liver organoid or liver bud is selected as cells contained in the second matrix, for example, vascular cells, preferably vascular endothelial cells, and more preferably hemogenic endothelial cells (HECs) can be selected as a cell contained in the first matrix.

One representative example of the organoid used in the present invention is a "pancreatic organoid". A production method for a pancreatic organoid is known, and as the pancreatic organoid used in the present invention, pancreatic organoids obtained by various known production methods can be used.

The pancreatic organoid is preferably a "pancreatic bud". A production method for a pancreatic bud is also known, and for example, as described in Patent Literature 1 mentioned above, a pancreatic bud can be produced from a combination of pancreatic β cells, vascular endothelial cells and mesenchymal stem cells. It is noted that a pancreatic β cell corresponds to a differentiated cell of a parenchymal cell used herein, and that a vascular endothelial cell and a mesenchymal cell correspond to an undifferentiated cell of a non-parenchymal cell used herein.

In the present invention, on the basis of known information on production methods for organoids of various organs (see, for example, http://www.amsbio.com/brochures/organoid-culture-handbook.pdf), an organoid that can be embedded in the second matrix can be precedently produced. It is noted that a production method employed here can be utilized also as a basic production method for a portion excluding the structure peculiar to the present invention in forming organoids of various organs from cells embedded in the second matrix.

Hardness of the second matrix can be appropriately adjusted in consideration of permeability of, for example, oxygen supplied from a gas phase, or a substance such as a component supplied from a liquid medium, and another action on growth of cells or organoid contained in the second matrix, and can be set to, for example, a range of 0.05 to 50 kPa. It is noted that an index of this "hardness" can be appropriately converted into a dilution rate in diluting Matrigel with a medium, or a concentration of an ECM in the matrix. Besides, a thickness of the second matrix, an area of a contact surface with the first matrix (and the third matrix provided if necessary) and the like can be appropriately adjusted in consideration of matters similar to those described above.

—Third Matrix

The third matrix used if necessary does not contain cells, an organoid and the like so that the cells contained in the second matrix can efficiently receive oxygen and the like permeating through the third matrix. As long as this function is fulfilled, however, the third matrix is allowed to contain, for example, a substance affecting culture of the cells contained in the first matrix, or the cells and/or the organoid contained in the second matrix. For example, when vascular cells (such as vascular endothelial cells) are contained in the first matrix, the third matrix positioned to oppose the first matrix with the second matrix disposed therebetween is caused to contain VEGF, so that a blood vessel formed by the vascular cells can easily extend in a direction toward (the cells contained in) the second matrix.

Hardness of the third matrix can be appropriately adjusted in consideration of permeability of, for example, oxygen and another substance, and the like, and can be set to, for example, a range of 0.05 to 50 kPa. It is noted that an index of this "hardness" can be appropriately converted into a dilution rate in diluting Matrigel with a medium, or a concentration of an ECM in the matrix. Besides, a thickness of the third matrix, an area of a contact surface with the second matrix and the like can be appropriately adjusted in consideration of items similar to those described above.

Figure 2:
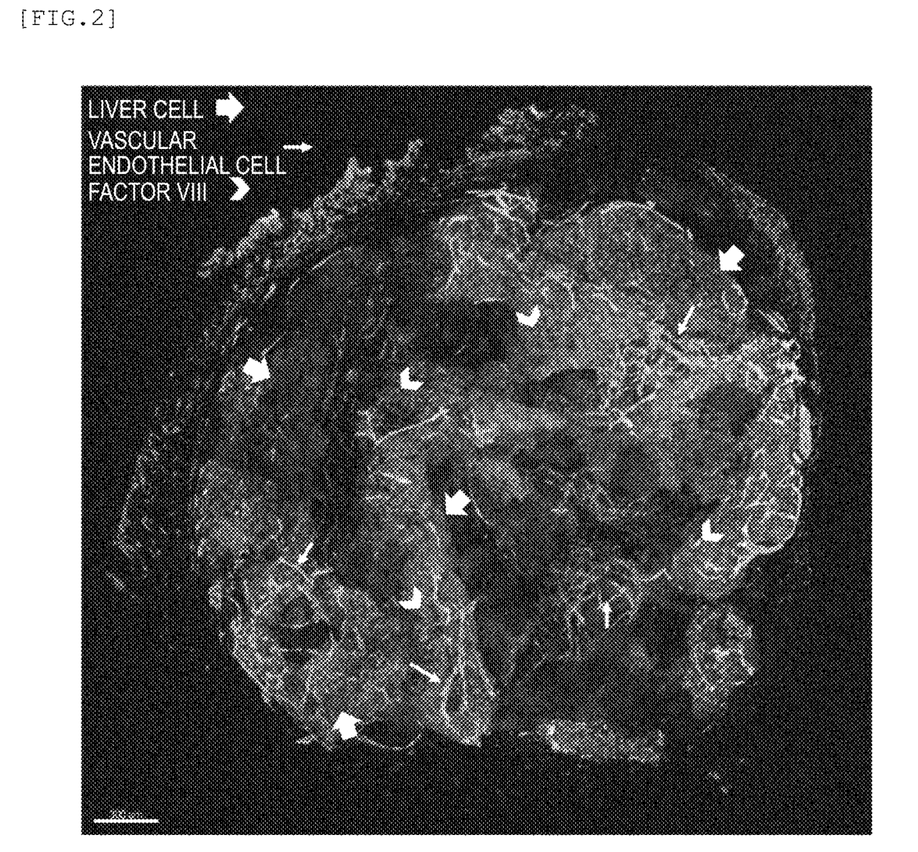
FIG. 2 is a microscope photograph of a "hierarchical cell network" found inside a matrix composition produced by the present invention.

The matrix composition of the present invention preferably contains a "hierarchical cell network". The term "hierarchical cell network" means, for example, in regard to a vascular network constructed by vascular endothelial cells, a state where a directional vascular network formed by vascular endothelial cells contained in the first matrix is formed separately from a vascular network having poor directionality (extending in a disordered manner) and formed by vascular endothelial cells contained in an organoid in the second matrix, and a "hierarchical" cell network (vascular network) of the former and latter networks is formed in the whole matrix composition (see FIG. 2).

The above-described matrix composition of the present invention may be obtained any production method. As a suitable production method, a production method for a matrix composition of the present invention described below can be employed.

Production Method for Matrix Composition—

The production method for a matrix composition of the present invention includes at least the following steps (a) and (b), and if necessary, further includes the following step (c):

(a) of suspending, in a second matrix in a fluid form, cells constituting an organ and/or an organoid, and solidifying the second matrix;

(b) of suspending, in a first matrix in a fluid form, cells selected from the group consisting of vascular cells, nerve cells, and blood cells, covering the second matrix with the first matrix in such a manner that the first matrix has at least one opening, and solidifying the first matrix; and (c) of immersing, in a liquid medium, a matrix composition obtained through the steps (a) and (b) in a state of being suspended from a breathable membrane for culturing, with gas exchange through the breathable membrane ensured, to cause the cells constituting an organ contained in the second matrix to form a conformational structure.

In the step (a), a method for suspending the cells constituting an organ or the like in the second matrix in a fluid form is not especially limited. For example, when a mixture of Matrigel and a medium is used as the matrix, a suspension to be used in the step (a) can be obtained by mixing Matrigel and the medium at a low temperature (of, for example, 4° C.) at which Matrigel is in a fluid form, and mixing the resultant mixture with the cells constituting an organ or the like.

A method for solidifying the second matrix contained in the suspension for the step (a) is not especially limited. For example, when a mixture of Matrigel and a medium is used as the matrix for preparing the suspension for the step (a), a solidified product of the suspension can be obtained by heating the suspension up to a temperature (of, for example, 37° C.) where the Matrigel is solidified (gelled).

In the step (b), a method for suspending vascular cells or the like in the first matrix in a fluid form, and a method for solidifying the first matrix are not also especially limited, and these methods can be respectively performed similarly to the suspension method and the solidification method of the step (a) described above.

As a method for "covering the second matrix with the first matrix in such a manner that the first matrix has at least one opening, and solidifying the first matrix", it is possible to employ, for example, a method in which the second matrix containing the prescribed cells is first dropped onto the breathable membrane to be solidified, and the first matrix containing the prescribed cells or the like is subsequently dropped onto the solidified second matrix to be solidified. A contact portion between the second matrix and the breathable membrane is not covered with the first matrix, and corresponds to the opening.

Besides, in an embodiment using the third matrix described above, it is possible to employ a method in which the third matrix not containing cells is first directly dropped onto the breathable membrane to be solidified, the second matrix containing the prescribed cells is subsequently dropped onto the solidified third matrix to be solidified, and the first matrix containing the prescribed cells or the like is finally dropped onto the solidified second matrix to be solidified. Thus, the third matrix is filled in the opening of the first matrix.

In the step (c), the term "breathable membrane" refers to a membrane having at least oxygen permeability, and having, if necessary, permeability of carbon dioxide or another desired gas, and various breathable membranes are known. Examples of the breathable membrane include membranes made of fibers of polyethylene terephthalate (PET), polydimethylsiloxane (PDMS), fluorocarbon, polytetrafluoroethylene (PTFE), polyurethane and the like. The breathable membrane may be, if necessary, subjected to a surface treatment for increasing or reducing cell attachment, such as a coating treatment with an ECM of collagen or the like. Besides, the breathable membrane may be a membrane (hybrid membrane) obtained by laminating a breathable membrane on a porous membrane (mesh) made of a fiber different from the breathable membrane, if necessary.

The matrix composition "in a state of being suspended from a breathable membrane" can be obtained by facing downward (to be upside down) the matrix composition attached to the breathable membrane and solidified, which is obtained through the above-described steps (a) and (b) including dropping the second matrix containing the prescribed cells or the like onto the breathable membrane (or with the third matrix precedently dropped) and the like. When the matrix composition in this state is immersed in a liquid medium held in a culture vessel with an appropriate member such as a holder, and the breathable membrane is not immersed to be in the air (or in a desired culture atmosphere), it is possible to "immerse the matrix composition in the liquid medium for culturing, with gas exchange through the breathable membrane ensured". A culture period may be a period sufficient for "causing the cells constituting an organ contained in the second matrix to form a conformational structure", and preferably a period also sufficient for the vascular cells or the like contained in the first matrix to form a hierarchical structure.

The liquid medium for the step (c) may be a medium suitable for culturing vascular cells or the like contained in the first matrix, and cells constituting an organ and/or an organoid contained in the second matrix. Those skilled in the art can prepare a medium by selecting, depending on the cells or the organoid to be cultured, appropriate type and amount of basal medium, and an additive used if necessary, and mixing these. Besides, since each of the first matrix and the second matrix contains a plurality of types of (at least two types of) cells, a medium obtained by mixing, in an appropriate ratio, basal media and necessary additives for culturing these cells can be used. In particular, when the second matrix contains a plurality of types of cells for forming an organoid (for example, a liver bud), or contains an organoid already formed, a medium having a composition suitable for formation and/or growth of the organoid is suitably used.

Examples of a basal medium for a vascular endothelial cell include DMEM/F-12(Gibco), Stempro-34 SFM (Gibco), Essential 6 medium (Gibco), Essential 8 medium (Gibco), EGM (Lonza), BulletKit (Lonza), EGM-2 (Lonza), BulletKit (Lonza), EGM-2 MV (Lonza), VascuLife EnGS Comp Kit (LCT), Human Endothelial-SFM Basal Growth Medium (Invitrogen), and Human Microvascular Endothelial Cell Growth Medium (TOYOBO). Examples of an additive for a vascular endothelial cell include one or more selected from the group consisting of B27 Supplements (Gibco), BMP4 (bone morphogenetic protein 4), GSK β inhibitor (for example, CHIR99021), VEGF (vascular endothelial cell growth factor), FGF2 (fibroblast growth factor (also designated as bFGF (basic fibroblast growth factor))), Folskolin, SCF (stem cell factor), TGF β receptor inhibitor (for example, SB431542), Flt-3L (Fms-related tyrosine kinase 3 ligand), IL-3 (interleukin 3), IL-6 (interleukin 6), TPO (thrombopoietin), hEGF (recombinant human epithelial cell growth factor), hydrocortisone, ascorbic acid, IGF1, FBS (fetal bovine serum), an antibiotic (for example, gentamicin or amphotericin B), heparin, L-glutamine, phenol red and BBE.

Examples of a basal medium for a hepatocyte include RPMI (Fujifilm Corporation) and HCM (Lonza). Examples of an additive for a hepatocyte include one or more selected from the group consisting of Wnt3a, activin A, BMP4, FGF2, FBS, HGF (hepatocyte growth factor), oncostatin M (OSM) and dexamethasone (Dex). To a medium for a hepatocyte, at least one selected from ascorbic acid, BSA-FAF, insulin, hydrocortisone and GA-1000 can be added if necessary. More specifically, examples of the medium for a hepatocyte include a medium obtained by removing hEGF (recombinant human epithelial cell growth factor) from HCM BulletKit (Lonza); and a medium obtained by adding 1% B27 Supplements (Gibco) and 10 ng/mL hHGF (Sigma-Aldrich) to PRMI1640 (Sigma-Aldrich). In particular, when a liver bud is to be produced, for example, a medium obtained by adding dexamethasone, oncostatin M and HGF to a medium obtained by mixing, in a ratio of 1:1, EGM BulletKit (Lonza) and HCM BulletKit (Lonza) from which hEGF (recombinant human epithelial cell growth factor) has been removed can be used.

Examples of a basal medium for a pancreatic β cell include CMRL 1066 (Corning) and MCDB 131 (Gibco). Examples of an additive for a pancreatic β cell include Alk5 inhibitor II, T3 (L-3,30,5-triiodothyronine), Trolox, N acetyl cysteine, R428 (AXL inhibitor) and heparin. More specifically, an example of a medium for a pancreatic β cell includes a medium obtained by adding 10% FBS, 10 µM Alk5 inhibitor II and 1 µM T3 to CMRL basal medium. In particular, when a pancreatic organoid is to be produced, for example, a medium obtained by adding 1% B27 Supplements (Gibco), 0.2% BSA and 10 µM nicotinamide to a medium obtained by mixing, in a ratio of 1:1, EGM BulletKit (Lonza) and DMEM/F-12 (Gibco) can be also used.

The culture vessel holding the liquid medium may be a vessel in accordance with the shape, the size and the like of the matrix composition, and for example, a plate having a plurality of wells can be used. Preferably, the culture vessel has a surface made of a material to which the matrix does not attach, or has a surface-treated surface, and for example, a commercially available low-attachment culture vessel can be used.

Culture conditions (such as an atmosphere, a culture temperature and a culture period) employed in the step (c) can be appropriately adjusted in accordance with the composition of the cells constituting an organ contained in the second matrix so that a conformational structure (or an organ bud) can be formed. For example, the culture in the step (c) can be performed in 5% $CO_2$ at 30 to 40° C. (preferably at about 37° C.) for 1 to 10 days (for example, for 1 to 3 days for a liver bud).

Formation of the conformational structure (three-dimensional structure) can be checked by visual observation or microscopic observation. Besides, production of an organoid can be determined by, in addition to the formation of a conformational structure, whether or not a prescribed cell marker, and a marker of a parenchymal cell of an organ in particular, is positive, and preferably whether or not a protein of the marker is secreted into a culture supernatant. In production of, for example, a liver organoid or a liver bud, whether or not expression of a marker such as HHEX, SOX2, AFP, ALB or HNF4a is positive, or whether or not ALB (albumin) is secreted into a culture supernatant can be employed as the criterion. In production of a pancreatic organoid or a pancreatic bud, whether or not expression of a marker such as PDX1, SOX17 or PSX9 is positive can be employed as the criterion.

In another aspect of the present invention, the production method for a matrix composition of the present invention can be modified to an embodiment using a "substance permeable membrane" instead of the "breathable membrane" in the step (c). In other words, in the modified embodiment, the second matrix receives, through another liquid medium (herein referred to as the "second liquid medium") different from the liquid medium where the convex matrix is immersed (herein referred to as the "first liquid medium") and the "substance permeable membrane", a nutrient and another additive component, and a gas such as oxygen dissolved in the second liquid medium instead that it receives oxygen, carbon dioxide and another gas directly or indirectly via the third matrix provided if necessary, through the "breathable membrane" exposed to a gas phase. In this case, it is suitable that the second liquid medium is in contact with (performs material exchange with) only the second matrix or the third matrix via the substance permeable membrane and is not in contact with (does not perform material exchange with) the first liquid medium via the substance permeable membrane, namely, that the whole surface of the "substance exchange membrane" is coated with the second matrix or the third matrix.

The "substance permeable membrane" is a membrane that blocks permeation of cells but ensures permeation of a desired substance. Such a substance permeable membrane is known, and an example includes a membrane made of collagen or polydimethylsiloxane (PDMS).

In the aspect described above, the step (c) of the production method for a matrix composition of the present invention can be changed to, for example, the following step of:

(c') immersing, in a first liquid medium, a matrix composition obtained through the steps (a) and (b) in a state of being in contact with a substance permeable membrane for culturing, with material exchange with a second liquid medium through the substance permeable membrane ensured, to cause the cells constituting an organ contained in the second matrix to form a conformational structure.

Besides, also in a system of the present invention described later, description regarding the step (c) can be replaced by description regarding the step (c').

—Production Method for Chimeric Non-human Animal—

A production method for a chimeric non-human animal of the present invention includes transplanting the matrix composition of the present invention or the matrix composition obtained by the production method for a matrix composition of the present invention in a non-human animal for differentiation into a tissue or an organ.

The matrix composition obtained by the production method for a matrix composition of the present invention including the step (c) is formed on the breathable membrane, and when the matrix composition is to be transplanted in a non-human animal, the breathable membrane may be peeled off to transplant the matrix composition alone. Alternatively, a biodegradable material may be used for the breathable membrane.

Examples of the non-human animal include a mouse, a rabbit, a pig, a dog and a monkey.

A chimeric non-human animal of the present invention is a chimeric non-human animal obtained by the above-described production method, namely, a non-human animal having a tissue or an organ having been differentiated from the matrix composition of the present invention or the matrix composition obtained by the production method for a matrix composition of the present invention transplanted therein.

The chimeric non-human animal of the present invention can be used for, for example, a method for evaluating a drug such as prediction of a drug metabolism profile, evaluation of drug efficacy, evaluation of toxicity, and evaluation of drug interaction in a human.

—Culture System—

A system of the present invention is a system for performing the production method for a matrix composition of the present invention, and particularly the step (c), and includes a matrix composition suspended from a breathable membrane, and a liquid medium in which the matrix composition is immersed.

The "matrix composition suspended from a breathable membrane" and the "liquid medium in which the matrix composition is immersed" prescribed in the system of the present invention are respectively those described above herein, and technical matters similar to those described in relation to the production method for a matrix composition of the present invention and the like can be applied.

The system of the present invention can further include, in addition to the above-described constituent elements, constituent elements necessary or preferable for practicing the present invention such as a tool for holding the breathable membrane from which the matrix composition is suspended, a tool for holding the liquid medium (for example, a plate having wells), and a culture apparatus for performing culture under a suitable atmosphere and temperature.

—Production Method for Plasma Protein—

A production method for a plasma protein of the present invention includes the following steps (1) and (2) of:

(1) culturing the matrix composition of the present invention; and (2) collecting a culture supernatant from a cultured product cultured in the step (1).

Examples of the "plasma protein" include a blood coagulation factor (for example, factor II, factor V, factor VII, factor VIII, factor IX, factor X and factor XI), an anti-blood coagulation factor (for example, antithrombin or the like), a complement (for example, C1 to C9, factor B, factor D, factor I, factor H or the like), an enzyme (for example, a1 antitrypsin or a lysosomal enzyme), and other proteins (for example, albumin). Examples of the lysosomal enzyme include α-mannosidase, α-fucosidase, α-galactosidase, α-glucosidase, β-galactosidase, β-glucosidase, β-hexosaminidase (for example, β-hexosaminidase A, β-hexosaminidase B or β-hexosaminidase S), β-glucuronidase, galactocerebrosidase, cathepsin (for example, cathepsin A, cathepsin B, cathepsin C, cathepsin D, cathepsin E, cathepsin K or the like), α-L-iduronidase, arylsulfatase, N-acetylgalactosamine-6-sulfatase, iduronate-2-sulfatase, heparan N-sulfatase, α-N-acetylglucosaminidase, acetyl CoA-α-glucosaminide N-acetyltransferase, N-acetylglucosamine-6-sulfatase, galactose-6-sulfatase, arylsulfatase A, B or C, arylsulfatase A cerebroside, α-N-acetylgalactosaminidase, α-neuramidase, aspartylglucosaminidase, acid lipase, acid ceramidase, sphingomyelinase, palmitoyl-protein thioesterase, tripeptidyl peptidase and β-mannosidase.

As the culturing method or another embodiment in the step (1), for example, the composition of the medium and the like can be set in accordance with the culturing method or another embodiment in the step (c) of the "production method for a matrix composition" of the present invention.

In one embodiment of the present invention, the medium used in the step (1) is a medium in which a serum concentration is adjusted to a proper range, and can be preferably a medium in which a serum concentration is 0% (namely, with no serum added to the medium) to 5%. It is noted that a "serum substitute" can be used instead of the "serum", and in this case, a concentration range of the serum substitute can be set to one corresponding to the concentration range of the serum.

In one embodiment of the present invention, the medium used in the step (1) is a medium supplemented with a Nrf2 (nuclear factor erythroid-2-related factor 2) activator. Examples of the Nrf2 activator include R-α-lipoic acid, tert-butylhydroquinone, sulforaphane, a *Polygonum cuspidatum* extract containing resveratrol, and BM (bardoxolone methyl). An amount of the Nrf2 activator to be added can be appropriately determined by those skilled in the art, and is preferably 20 nM or more.

Culture conditions (such as an atmosphere, a culture temperature, and a culture period) employed in the step (1) can be appropriately adjusted so that a desired culture supernatant can be collected in the step (2), and for example, the culture can be performed in 5% $CO_2$ at 30 to 40° C. (preferably at about 37° C.) usually for 10 to 50 days. It is noted that a culture period in the step (1) until collection of a culture supernatant is usually longer than a culture period in the step (c) until formation of an organoid (for example, an organ bud), and can be set to a period until a production amount (concentration in the culture supernatant) of the plasma protein reaches a desired level.

Detection and quantitative determination of the plasma protein such as a blood coagulation factor or a complement can be performed by a known method, for example, by ELISA (enzyme-linked immuno sorbent assay), and kits for this purpose [for example, Human Coagulation Factor II (F2) ELISA Kit (Biomatik), Human Coagulation Factor V (F5) ELISA Kit (Biomatik), Human Coagulation Factor VII (F7) ELISA Kit (Biomatik), Human Coagulation Factor VIII (F8) ELISA Kit (Biomatik), Human Coagulation Factor IX (F9) ELISA Kit (Biomatik), Human Coagulation Factor X (F10) ELISA Kit (Biomatik), Human Coagulation Factor XI (F11) ELISA Kit (Biomatik), High Sensitive Human Albumin (ALB) ELISA Kit (Biomatik), and for (C3): Complement C3 Human ELISA kit (Abcam), for (C5): Complement C5 Human ELISA kit (Abcam), Human Factor H ELISA Kit (Abcam) and Human Factor B ELISA Kit (Abcam)] are commercially available.

By the production method of the present invention, a plasma protein usable for treatment and the like of various diseases can be produced. More specifically, by the step (2) of the production method for a plasma protein of the present invention, it is possible to collect, for example, a culture supernatant that contains a plasma protein such as a blood coagulation factor, a complement, an a1 antitrypsin (AAT) or a lysosomal enzyme in a concentration preferable for producing a composition for treating diseases caused by defect, deficiency, abnormality, activity decrease or the like of these plasma proteins. The culture supernatant thus obtained is low in toxicity (for example, acute toxicity, chronic toxicity, genetic toxicity, reproductive toxicity, cardiotoxicity or carcinogenicity), and can be formulated directly or with an additive used for a medicament added.

Specific examples of a disease related to a blood coagulation factor (blood coagulation disease) include hemophilia (hemophilia A (factor VIII deficiency) or hemophilia B (factor IX deficiency)), hemophilia-related diseases (factor II deficiency, factor V deficiency, factor VII deficiency, factor X deficiency or factor XI deficiency), and thrombosis (antithrombin deficiency).

Specific examples of a disease related to a complement (complement abnormalities) include C3 deficiency, C5 deficiency, factor B deficiency and factor H deficiency.

A specific example of a disease related to a1 antitrypsin (AAT) includes AAT deficiency.

Specific examples of a disease related to lysosome (lysosomal disease) include aspartylglucosaminuria, Fabry disease, juvenile Batten disease (CNL1), classic late infantile Batten disease (CNL2), Farber disease, fucosidosis, galactosialidosis, 1, 2 or 3 Gaucher disease, GM1-gangliosidosis, Hunter syndrome, Hurler syndrome, Hurler-Scheie syndrome, Scheie syndrome, Krabbe disease, α-mannosidosis, β-mannosidosis, Maroteaux-Lamy syndrome, metachromatic leukodystrophy, Morquio syndrome A, Morquio syndrome B, mucolipidosis II/III, Niemann-Pick disease type A or B, Pompe disease, Sandhoff disease, Sanfilippo syndrome type A, Sanfilippo syndrome type B, Sanfilippo syndrome type C, Sanfilippo syndrome type D, Schindler disease, Schindler Kanzaki disease, sialidosis, Sly syndrome, Tay-Sachs disease, Wolman disease, mucopolysaccharidosis IX, multiple sulfatase deficiency, Danon disease, free sialic acid storage disorders and ceroid lipofuscinosis.

For the above-described formulation, the production method for a plasma protein of the present invention may further include, if necessary, a step (3) of concentrating the culture supernatant collected in the step (2). The concentrated culture supernatant can be preferably used, for example, as a composition for treating blood coagulation diseases and/or complement abnormalities because it increases activity based on activated partial thromboplastin time (APTT) (shortens APTT), or as a composition for treating lysosomal diseases (for example, mucolipidosis II or mucolipidosis III) because it contains a plurality of enzymes at high concentrations owing to the concentration.

EXAMPLES

[Example 1] Production of Matrix Composition Containing Hemogenic Endothelial Cells and Cells Constituting Liver

[Experimental Method]

[1] Production of Human Non-hemogenic Endothelial Cells

Human iPS cells (1383D2; Center for iPS Cell Research and Application, Kyoto University) were cultured in DMEM/F-12 (Gibco) (10 ml) supplemented with 1% B-27 Supplements (Gibco), BMP4 (25 ng/ml) and CHIR99021 (8 µM) in 5% $CO_2$ at 37° C. for 3 days to induce mesoderm cells. The mesoderm cells thus obtained were further cultured in Stempro-34 SFM (Gibco) (10 ml) supplemented with VEGF (200 ng/ml) and Folskolin (2 µM) in 5% $CO_2$ at 37° C. for 7 days to obtain a CD31-positive, CD73-positive and CD144-positive human non-hemogenic endothelial cell population.

[2] Production of Human Hemogenic Endothelial Cells

Human iPS cells (625A4; Center for iPS Cell Research and Application, Kyoto University) were cultured in AK02N (Ajinomoto Co., Inc.) (8 ml) in 5% $CO_2$ at 37° C. for 6 to 7 days to form iPS cell colonies having a diameter of 500 to 700 µm. The colonies thus obtained were cultured in Essential 8 medium (Gibco) (8 ml) supplemented with BMP4 (80 ng/ml), VEGF (80 ng/ml) and CHIR99021 (2 µM) in 5% $CO_2$ at 37° C. for 2 days. Subsequently, the medium was exchanged with Essential 6 medium (Gibco) (8 ml) supplemented with VEGF (80 ng/ml), FGF2 (25 ng/ml), SCF (50 ng/ml) and SB431542 (2 µM), and the resultant was further cultured in 5% $CO_2$ at 37° C. for another 2 days to induce lateral plate mesoderm cells. Thereafter, the medium was exchanged with Stempro-34 SFM (Gibco) (8 ml) supplemented with VEGF (80 ng/ml), SCF (50 ng/ml), Flt-3L (50 ng/ml), IL-3 (50 ng/ml), IL-6 (50 ng/ml) and TPO (5 ng/ml), and the resultant was cultured in 5% $CO_2$ at 37° C. for 2 days. The medium was further exchanged with a medium obtained by removing VEGF from the medium having the above-described composition, and the resultant was cultured in 5% $CO_2$ at 37° C. for 1 day to obtain a CD34-positive and CD73-negative hemogenic endothelial cells.

[3] Production of Human Liver Endoderm Cells

Human iPS cells (1383D2; Center for iPS Cell Research and Application, Kyoto University) were cultured in a basal medium, RPMI (Fujifilm Corporation) (2 ml) supplemented with Wnt3a (50 ng/mL) and activin A (100 ng/ml) in 5% $CO_2$ at 37° C. for 5 days to induce endoderm cells. The endoderm cells thus obtained were cultured with 1% B27 Supplements (Gibco) and FGF 2 (10 ng/ml) added to the basal medium in 5% $CO_2$ at 37° C. for another 5 days to obtain AFP-positive, ALB-positive and HNF4α-positive human liver endoderm cell population.

[4] Production of Human Mesenchymal Cells

Human iPS cells (1383D2; Center for iPS Cell Research and Application, Kyoto University) were cultured in a basal medium, DMEM/F-12 (Gibco) (10 ml) supplemented with 1% B-27 Supplements (Gibco), BMP4 (25 ng/ml) and CHIR99021 (8 µM) in 5% $CO_2$ at 37° C. for 3 days to induce mesoderm cells. The mesoderm cells thus obtained were cultured with PDGFBB and activin A added to the medium in 5% $CO_2$ at 37° C. for another 3 days. The cultured cells were collected and seeded again in a new gelatin-coated plate, and cultured with bFGF and BMP4 added to the basal medium in 5% $CO_2$ at 37° C. for another 4 days to obtain FOXF1-positive, COL4A-positive, ALCAM-positive and CD73-positive human mesenchymal cell population.

[5] Cell Embedding in Extracellular Matrix and Production of Matrix Composition

A medium containing a liver induction medium obtained by adding FBS, HGF, OSM and Dex to HCM (manufactured by Lonza) and EGM (Lonza) mixed in a volume ratio of 1:1 (herein, referred to as the "organoid medium") was prepared. Besides, the organoid medium and Matrigel (BD Pharmingen) were mixed in a volume ratio of 1:1 to prepare a matrix (herein, referred to as the "organoid medium/Matrigel mixed matrix").

5 µL of the organoid medium/Matrigel mixed matrix was dropped onto an inverted PET Millicell Hanging Cell Culture Insert (Millipore) and solidified by heating the resultant to 37° C., and thus, a "third matrix" of the present invention was formed.

The human liver endoderm cells, the human non-hemogenic endothelial cells and the human mesenchymal cells produced as described above were mixed in a ratio of 10:7:1 with the organoid medium/Matrigel mixed matrix at 4° C. 3 µL of the thus obtained mixture was dropped onto the third matrix solidified as described above, and the resultant was solidified by heating to 37° C., and thus, a "second matrix" of the present invention was formed.

Besides, the human hemogenic endothelial cells produced as described above were mixed with the organoid medium/Matrigel mixed matrix at 4° C. 8 µL of the thus obtained mixture was dropped onto the second matrix solidified as described above, and the resultant was solidified by heating to 37° C., and thus, a "first matrix" of the present invention was formed.

To a low-attachment 24-well plate, 600 μL of the organoid medium supplemented with VEGF (80 ng/ml), SCF (50 ng/ml), Flt-3L (50 ng/ml), IL-3 (50 ng/ml), IL-6 (50 ng/ml) and TPO (5 ng/ml) was added. A matrix composition containing the first to third matrices having been solidified on the hanging drop insert as described above was inserted toward the medium in the well. The medium was exchanged by half every day until day 4 after starting the culture, and was exchanged once every 2 or 3 days thereafter. A culture fluid was collected over time until about day 21 to 42 of the culture to measure production amounts of a coagulation factor and a complement factor.

[Results]

An amount of a coagulation factor (factor VIII) produced and amounts of complement factors (complement C3, complement C5, factor B and factor H) produced contained in the culture fluid collected on day 21 of the culture are shown in Table 1.

TABLE 1

| Example | | Amount of Production of Plasma Protein (ng/million cells; Mean ± S.E.) | | | | |
|---|---|---|---|---|---|---|
| | | Factor VIII (on day 21) | C3 (on day 21) | C5 (on day 21) | FB (on day 21) | FH (on day 21) |
| 1 | First Matrix: Human Hemogenic Endothelial Cells, Second Matrix: Human Liver Endoderm Cells:Human Non-hemogenic Endothelial Cells:Human Mesenchymal Cells = 10:7:1, Third Matrix: no cells | 572.2 ± 19.1 | 1754.7 ± 268.7 | 268.5 ± 37.6 | 503.5 ± 59.8 | 952.3 ± 67.4 |

The invention claimed is:

1. A matrix composition, comprising:
   (1) a first matrix containing one or more cells selected from the group consisting of vascular cells, nerve cells, and blood cells;
   (2) a second matrix containing cells constituting an organ and/or an organoid; and
   (3) a third matrix not containing cells,
   wherein the first matrix envelops the second matrix, and the first matrix has at least one opening which is a portion of the first matrix that does not envelop the second matrix and the at least one opening is closed by the third matrix.

2. The matrix composition according to claim 1, wherein the matrix composition has a hierarchical cell network.

3. The matrix composition according to claim 1, wherein the vascular cells contained in the first matrix is hemogenic endothelial cells.

4. The matrix composition according to claim 1, wherein the cells constituting an organ contained in the second matrix is a combination of liver endoderm cells, vascular endothelial cells and mesenchymal stem cells, or a combination of pancreatic β cells, vascular endothelial cells and mesenchymal stem cells.

5. A production method for the matrix composition according to claim 1, comprising the steps of:
   (a) suspending, in a second matrix in a fluid form, cells constituting an organ and/or an organoid, and solidifying the second matrix; and
   (b) suspending, in a first matrix in a fluid form, cells selected from the group consisting of vascular cells, nerve cells and blood cells, covering the second matrix with the first matrix in such a manner that the first matrix has at least one opening for supplying oxygen to the second matrix, wherein the at least opening is a portion of the first matrix that does not envelop the second matrix and the at least one opening is closed by a third matrix not containing cells, and solidifying the first matrix.

6. The production method according to claim 5, further comprising a step of:
   (c) immersing, in a liquid medium, the matrix composition in a state of being suspended from a breathable membrane for culturing, with gas exchange through the breathable membrane ensured, to cause the cells constituting an organ contained in the second matrix to form a conformational structure.

7. A production method for a chimeric non-human animal, comprising transplanting the matrix composition according to claim 1 in a non-human animal for differentiation into a tissue or an organ.

8. A culture system, comprising:
   a matrix composition suspended from a breathable membrane; and
   a liquid medium in which the matrix composition is immersed,
   wherein the matrix composition contains:
   (1) a first matrix containing one or more cells selected from the group consisting of vascular cells, nerve cells, and blood cells;
   (2) a second matrix containing cells constituting an organ and/or an organoid; and
   (3) a third matrix not containing cells,
   wherein the first matrix envelops the second matrix, and the first matrix has at least one opening which is a portion of the first matrix that does not envelop the second matrix and the at least one opening is closed by the third matrix.

9. A production method for a plasma protein, comprising the steps of:
   (1) culturing the matrix composition according to claim 1; and
   (2) collecting a culture supernatant from a cultured product cultured in the step (1).

10. A production method for a chimeric non-human animal, comprising transplanting the matrix composition produced by the method according to claim 5 in a non-human animal for differentiation into a tissue or an organ.

* * * * *